(12) United States Patent
Howard et al.

(10) Patent No.: US 6,168,802 B1
(45) Date of Patent: *Jan. 2, 2001

(54) COMPOSITIONS CONTAINING CREATINE AND ALOE VERA EXTRACT

(75) Inventors: Alan Norman Howard, Cambridge; Roger Harris, Suffolk, both of (GB)

(73) Assignee: The Howard Foundation, Cambridge (GB)

( * ) Notice: Under 35 U.S.C. 154(b), the term of this patent shall be extended for 0 days.

This patent is subject to a terminal disclaimer.

(21) Appl. No.: 09/324,119

(22) Filed: Jun. 2, 1999

Related U.S. Application Data

(63) Continuation-in-part of application No. 08/866,517, filed on May 30, 1997, now Pat. No. 5,968,544.

(30) Foreign Application Priority Data

May 31, 1996 (GB) .................................... 9611356

(51) Int. Cl.[7] .............. A61K 9/08; A61K 9/10; A61K 9/14
(52) U.S. Cl. ............ 424/439; 424/195.1; 424/489; 514/937; 514/970; 514/773; 514/777
(58) Field of Search ................... 424/439, 489, 424/195.1; 426/69; 514/937, 970

(56) References Cited

U.S. PATENT DOCUMENTS

| 3,615,600 | 10/1971 | Tonsbeek | 99/140 N |
|---|---|---|---|
| 4,464,409 | 8/1984 | Rooij | 426/536 |
| 4,647,453 | 3/1987 | Meisner | 424/54 |
| 4,772,591 | 9/1988 | Meisner | 514/62 |
| 5,968,544 | * 10/1999 | Howard et al. | 424/439 |

FOREIGN PATENT DOCUMENTS

| 59025663 | 2/1984 | (EP) . |
|---|---|---|
| 0669083 | 2/1995 | (EP) . |
| 50087771 | 9/1996 | (JP) . |
| 94/02127 | 2/1994 | (WO) . |
| 94/15488 | 7/1994 | (WO) . |
| 94/17794 | 8/1994 | (WO) . |
| 96/04240 | 2/1996 | (WO) . |
| 96/14063 | 5/1996 | (WO) . |
| 96/36348 | 11/1996 | (WO) . |

* cited by examiner

*Primary Examiner*—James M. Spear
(74) *Attorney, Agent, or Firm*—Pillsbury Madison & Sutro LLP

(57) ABSTRACT

Disclosed are compositions which include creatine and Aloe Vera extract, for the purpose of increasing the creatine supply deposits of human beings, and to improve their intestinal health. The composition is presented as a drink, either constituted from a dry powder or in liquid form. Also disclosed is a method of increasing the stability of a drink or semi-liquid solid comprising creatine and Aloe Vera extract by storing the compositions below ambient temperature, preferably 0–8° C.

17 Claims, No Drawings

COMPOSITIONS CONTAINING CREATINE AND ALOE VERA EXTRACT

This is a Continuation-in-Part application (MPEP 201.09) of National application Ser. No. 08/866,517 filed May 30, 1997 U.S. Pat. No. 5,968,544.

FIELD OF THE INVENTION

This invention relates to compositions for human consumption comprising creatine and Aloe Vera extract and to a method of providing stable creatine containing compositions.

BACKGROUND OF THE INVENTION

In the last few years there has been considerable interest among athletes in creatine, which occurs abundantly in skeletal muscle. Creatine plays a pivotal role in the regulation and homeostasis of skeletal muscle energy metabolism and it is now generally accepted that the maintenance of phospho-creatine availability is important to the continuation of muscle force production. Although creatine synthesis occurs in the liver, kidney and pancreas it has been known for sometime that the oral ingestion of creatine will add to the whole body creatine pool, and it has been shown that the ingestion of 20 to 30 g creatine per day for several days can lead to a greater than 20% increase in human skeletal muscle total creatine content. Thus, WO94/02127 discloses the administration of creatine in amounts of at least 15 g (or 0.2–0.4 g/kg body weight) per day, for at least 2 days, for increasing muscular strength.

In fact, it was subsequently found that after several days of supplementation (20 g per day) with creatine it takes no more than 2 to 3 g per day to maintain the saturation of body stores. Creatine supplementation in an appropriate dose can provide improvements to athletes involved in explosive events, which include all events lasting from a few seconds to a few minutes (such as sprinting, swimming, weight-lifting etc). Endurance performance in events lasting longer than about 30 minutes appears to be unaffected by creatine supplementation. Creatine is a normal food component and is not a drug and its use is not contrary to official regulations. The biggest benefits of supplementation can be experienced by the elderly, vegetarians or those who eat no meat or fish since these people tend to have low muscle creatine content.

Aloe Vera (*Aloe barbadensis*) is a member of the lily family and is a cactus like succulent plant that grows in warm frost free climates. Central American Mexican Indians used Aloe Vera for centuries as a remedy for burns, to prevent blisters, peptic and duodenal ulcers and all types of stomach and intestinal disorders, kidney infections, topical and gastric ulcers as well as to promote longevity. Today Aloe Vera is becoming very popular and its benefits are scientifically recognized.

For the sake of clarity, the term Aloe Vera is used to refer to the plant and Aloe Vera extract to refer to compositions prepared by processing Aloe Vera (e.g. mashing, pulping, cutting, juicing and the like). Aloe Vera juice refers to the watery gel-like substances contained within Aloe Vera plants. Thus, Aloe Vera juice is one particular example of an Aloe Vera extract.

The main use of Aloe Vera in the past has been to prevent inflammation, particularly to the skin, especially after burns. But there are many other uses. Experiments and research studies have shown that after using Aloe Vera juice, the output of the digestive enzymes and the bacterial population of the intestines are improved. Thus there has been an increasing interest in Aloe Vera extract as a medicament to be taken orally as people become more acquainted with its medicinal properties Among the several methods of presentation, there is a growing use of Aloe Vera juice in soft drinks which are fruit flavored, and these are quite palatable. The inclusion of creatine in such a soft drink would be highly desirable because the Aloe Vera drink would be much more beneficial to health than an unsupplemented ordinary fruit drink.

Aloe Vera juice is acidic (commonly about pH3). Likewise, popular fruit drinks are in the region of pH 3–4 because the acidity gives the drink a pleasant 'bite' to the palate. It is well known that creatine is unstable in aqueous solutions at acid or neutral pH, and is converted into the related compound creatinine. This is highly significant as creatinine has no muscle performance-enhancing effect and is excreted from the human body as a waste product in urine. In view of the foregoing, EP 0 669 083 teaches that aqueous drinks for human consumption comprising creatine must be weakly alkaline, in order to prevent the conversion of creatine into creatinine, and this has become the generally accepted opinion.

Furthermore, creatine has been used in the past only for the preparation of products with a meaty or savory flavor. For instance, Tonsbeek (U.S. Pat. No. 3,615,600) discloses and is concerned with artificial flavoring mixtures which can impart a meaty flavor to foods. Similarly de Rooji (U.S. Pat. No. 4,464,409) is concerned with meat flavoring. Yamazak (JP-A-59035663) prepares a meat flavor by heating a mixture comprising creatine at pH 5.0–7.0 at temperature of 80–130° C. for 30–120 minutes. Under these conditions most of the creatine would be converted to creatinine.

It would be a great advantage to present a fruit flavored drink containing Aloe Vera extract, in which the creatine therein was substantially stable.

SUMMARY OF THE INVENTION

It is therefore a first object of the present invention to provide an acidic composition for human consumption, comprising creatine and Aloe Vera extract.

It is a second object of the present invention to provide a method of storing acidic liquid or semi-liquid compositions comprising creatine, for human consumption, at below ambient temperature.

Another object of the present invention to provide a method of supplying a creatine and Aloe Vera extract containing composition for human consumption, the method including providing a creatine and Aloe Vera extract containing acidic composition as a dry, stable powder which, when mixed with water or a suitable aqueous solution gives an acidic drink comprising physiologically effective quantities of creatine and in which the creatine is substantially stable.

Another object of the present invention is to provide a composition comprising creatine in substantially stable form, wherein the composition is suitable for human consumption and comprises solid creatine suspended in an edible matrix.

DETAILED DESCRIPTION OF THE INVENTION

In a first aspect the invention provides an acidic composition for human consumption, comprising creatine and Aloe Vera extract. The term acidic is intended to mean that the composition has a pH below 7.0. In particular the composition desirably has a pH between 2.5 and 6.5, preferably between 3.0 and 6.0. Typically the composition has a pH in the range 3.5–5.5 which, to the human palate, has a refreshingly sharp taste without being too acidic.

The creatine content of the composition may be present as any active form of creatine, (e.g. creatine phosphate) but creatine monohydrate is found particularly convenient as a source of creatine.

The Aloe Vera extract content of the composition may be present as an extract of the Aloe Vera plant, Aloe Vera juice, gel or lyophilized product such as those supplied commercially. Aloe Vera juice is 99.5% water and 0.5% solids. When the lyophilized form is used it is important to rehydrate with an appropriate amount of water.

The composition may be in the form of a dry powder or may be provided in liquid or semi-liquid form (e.g. as a drink or yogurt, respectively). In preferred embodiments the composition is a drink.

Surprisingly, the present inventors have found that the conversation of creatine to creatinine at acidic pH is actually sufficiently slow as to allow physiologically useful amounts of creatine to remain in the composition after considerable periods of time, such that creatine may be presented in acidic formulations, contrary to the teaching of the art. In particular, the conversion of creatine to creatinine can be greatly inhibited by storage of the compositions at lower than ambient temperatures (e.g. in commercial chiller cabinets at 0–8° C.).

Thus, in a second aspect the invention provides a method of storing an acidic liquid or semi-liquid compositions comprising creatine, for human consumption, the method comprising storage of the composition below ambient temperature, typically in a commercial chiller cabinet at 0–8° C. of the conventional sort familiar from any medium or large-sized food retailer. Typically the composition is an aqueous drink or a yogurt or similar semi-liquid foodstuff. The drink may be still or carbonated, and preferably comprises a fruit flavoring, such as citrus or berry.

Alternatively the composition may be provided as a dry powder which, upon mixing with (preferably dissolution in) a pre-determined volume of liquid (e.g. of substantially neutral pH) gives rise to an acidic solution. The creatine content of the composition is stable in the dry powder form at ambient temperature. Appropriate doses of the powder can then be dissolved, as required, to make up fresh drinks with the creatine content substantially undiminished. The powder may be dissolved in any liquid (e.g. water, milk) or semi-liquid (e.g. yogurt).

Accordingly, in a further aspect the invention provides a method of supplying a creatine and Aloe Vera extract containing composition for human consumption, the method comprising providing a creatine and Aloe Vera extract containing acidic composition as a dry, stable powder which, when mixed with water or a suitable aqueous solution gives an acidic drink comprising physiologically effective quantities of creatine and in which the creatine is substantially stable.

The term substantially stable is herein defined as a composition in which at least 75% of the original creatine in the composition is unchanged into creatinine for a period of at least 6 hours.

Typically, the powder is such that, when a certain amount is dissolved in a pre-determined volume of water, it provides a drink. Desirably, the powder is provided as unitary doses (of about 10–20 g) which may be dissolved in 200–350 mls of water to provide a drink. The unitary doses are conveniently supplied individually packaged in sachets, bags, packets, cylinders, bottles or other suitable packaging means. Preferably the package is hermetically sealed (e.g. a thin foil sachet) to prevent the ingress of water or water vapor. In some embodiments it may be desired to provide with the package a volumetric measuring means to allow a user to measure out an appropriate volume of water in which to dissolve the contents of the package. Typically this may take the form of a watertight container (e.g. of plastics material) with one or more graduations to indicate a certain volume. The container may take the form of a beaker or similar vessel, to hold water in which the composition may be dissolved, and from which the resulting solution may be drunk.

The composition will preferably comprise one or more further components to improve its palatability, stability, flavor or nutritive quality. These further components may include electrolytes, as already mentioned above, or may be selected from the group consisting of: vitamins, lipids, carbohydrates, amino acids, trace elements, colorings, flavors, artificial sweeteners, natural health improving substances, anti-oxidants, stabilizers, preservatives, and buffers.

Vitamins may be included with advantage in the composition of the invention. The following vitamins may be added in amounts which range from 20 to 100% of their recommended daily allowance (RDA). The following are typical of those which are useful: vitamin E, vitamin C, thiamin, riboflavin, niacin, vitamin B6, folacin, vitamin B12, biotin, and pantothenic acid.

In some cases a lipid component may be desirable. The carbohydrate content (if any) or the composition may be present as starch (particularly soluble starch) and/or sugars. The sugars which may be present in the composition include glucose, fructose, sucrose, and maltrose.

Artificial sweeteners which can be used include Aspartame, Acesulfam K, Saccharin and Cyclamate. Almost any desired flavoring can be added, most preferably fruity flavors such as berry, lemon, orange, papaya and grapefruit. Citric acid may also be used as an acidulant and as a buffering agent. Also other natural health improving substances may be added in physiologically active amounts. The following are typical of those which are useful: Pan D'Arco tea, Ginseng, Suma tea, Ginkgo, Bee Pollen, Myrrh.

Preservatives can be provided typically by potassium benzoate and/or potassium sorbate.

Coloring can be provided, typically by using a cold water soluble colorant such as beta-carotene. Other suitable colorings will be apparent to those skilled in the art.

A clouding agent may be included in the composition to improve the appearance of the finished drink and distinguish it from lemonade.

The mineral and trace elements can also be added in any type or form which is suitable for human consumption. It is convenient to provide the calcium and potassium in the form of their glucondates, phosphates or hydrogen phosphates, and magnesium as the oxide or carbonate, chromium as chromium picolmate, selenium as sodium selenite or selenate, and zinc as zinc gluconate. Typically the amounts are: sodium at 400 mg/liter, calcium at 100 mg/liter, chloride at 600 mg/liter, potassium at 200 mg/liter, magnesium at 75 mg/liter and phosphorus at 50 mg/liter, chromium at 125 µg/liter, selenium at 125 µg/liter and zinc at 15 mg/liter.

The amount of creatine per liter of prepared drink may range from 0.5 to 30 g, with a preferred content of about 12 g per liter. The normal serving size is in the range 250–330 ml, providing about 3 g of creatine. During the first 4 days of creatine supplementation the recommended consumption is 1.5 liters per day divided in 4 or 5 parts per day to achieve creatine saturation. This is followed by 1 drink of 250 ml per day containing 3 g of creatine to provide a maintenance level of creatine.

The amount of Aloe Vera extract (preferably juice) per liter of prepared drink may range from 20 ml to 1000 ml or about 0.1 g to 5 g lyophilized Aloe Vera solid. The normal serving size of 250–330 ml would provide 100–150 ml Aloe Vera juice, or about 0.5 to 0.75 g of lyophilized Aloe Vera solid.

In another aspect, the invention provides a composition comprising creatine in substantially stable form, wherein the composition is suitable for human consumption and comprises solid creatine suspended in an edible matrix.

This aspect of the invention is founded on the inventor's discovery that suspension of the creatine, substantially undissolved, in an edible matrix, preserves the creatine in substantially stable form and greatly inhibits the conversion of creatine to creatinine.

The edible matrix may be liquid, semi-liquid or solid. Particularly preferred are viscous liquids or spreadable solids.

In a preferred embodiment, the composition comprises a carbohydrate, such as a sugar. Further, in preferred embodiments the edible matrix may comprise a syrup, such as corn syrup, glucose syrup, honey, treacle and the like. Alternatively, the edible matrix may comprise a gel prepared from concentrated Aloe Vera extract.

If desired, the viscosity of the edible matrix and/or the composition as a whole, may be increased by the addition of viscosifiers, gelling agents and the like. Such components are well-known in the food industry and include, for example, plant-derived polysaccharides, gums and the like such as galactomannans, dextrans, guar gum, locust bean gum and so on.

A composition in accordance with the invention defined above may be such as to have any pH suitable for human consumption, but will generally have a pH below 7, typically in the range 2.5–6.5.

In preferred embodiment, the invention provides a composition which is acidic (i.e. has a pH below 7) and yet which may be stored above 4° C. (e.g. at ambient room temperature) whilst still being substantially stable with respect to the conversion of creatine to creatinine.

The present invention will be illustrated with reference to the following non-limiting examples:

EXAMPLE 1

This example describes the detailed formulation of an acidic composition in accordance with the invention.

The composition takes the form of a dry powder, which is to be dissolved in water to constitute a drink comprising creatine and Aloe Vera extract.

| | Ingredients |
|---|---|
| Dextrose Monohydrate | 300 g |
| Citric Acid | 32 g |
| Pectin (stabilizer) | 6.0 g |
| Salt | 5.0 g |
| Trisodium Citrate | 5.0 g |

| -continued | |
|---|---|
| | Ingredients |
| Beta Carotene | 3.0 g |
| Potassium Chloride | 2.9 g |
| Grapefruit Flavor | 2.9 g |
| Tricalcium Phosphate | 2.1 g |
| Heavy Magnesium Carbonate | 2.1 g |
| Vitamin Premix | 1.8 g |
| Lemon Flavor | 1.4 g |
| Orange Flavor | 1.4 g |
| Aspartame | 1.0 g |
| Creatine Monohydrate | 88 g |
| Lyophilized Aloe Vera | 17.6 g |

About 63 g of the above mixture when dissolved in 1 liter of water provides, per 150 ml serving, about 3 g creatine, 0.6 g Aloe Vera lyophilized solid (equivalent to 120 ml juice), energy kJ 203 (kcal 48), 11.1 g carbohydrate, 156 mg chloride, 100 mg sodium, 52 mg potassium, 26 mg calcium, 19.5 mg magnesium, 13 mg phosphorus, vitamins (vitamin E 3.4 mg, vitamin C 16.2 mg, Thiamin 0.3 mg, Riboflavin 0.4 mg, Niacin 5.0 mg, vitamin B6 0.4 mg, Folacin 85 μg, vitamin B12 0.9μg, Biotin 0.08 mg and Pantothenic acid 2.2 mg) and traces of protein, fat, and fiber. This provides a refreshing drink containing electrolytes, creatine and Aloe Vera extract which is relatively lower in calories than conventional drinks, and has a pH of about 3.8. The drink is also isotonic (i.e. corresponds to the osmoric potential of human body fluids) which is often preferred by sports people.

EXAMPLE 2

This example relates to another embodiment of the invention.

The formulation is as in example 1 above, except that the 300 g dextrose monohydrate is omitted and the aspartame content is increased to 2.5 g to compensate. When 5.3 g of this formulation is dissolved in 250 ml water, it provides an almost calorie free drink containing creatine and electrolytes which, is nutritionally useful to those wishing to lose or maintain their weight.

EXAMPLE 3

This example relates to a study of the stability of creatine at acid pH in a solution containing Aloe Vera juice.

Three drinks were examined, Aloe Vera Herbal Lemon (pH 3.72), Aloe Vera Natural (pH 3.68) and Aloe Vera Berry (pH 2.87). These were obtained from Aloe Commodities Int. inc, Farmers Branch, TX75234. All contained Aloe Vera juice as the major ingredient. The Aloe Vera Herbal lemon contained for example: organic Aloe Vera juice, purified water, natural lemon flavor, natural orange flavor, crystalline fructose, potassium gluconate, Chrome Mate™ (chromium picolinate), Pau D'Arco tea, Ginseng tea, Suma tea, Ginkgo tea, mint tea, bee pollen, ascorbic acid, zinc glucomate, selenium, myrrh, beta carotene, citric acid and less than 0.1% potassium benzoate and potassium sorbate as preservative. Aloe Vera Natural was a product containing primarily Aloe Vera juice mixed with purified water. Aloe Vera Berry contained berry juices as flavoring.

Creatine (0.569 g creatine, high-grade) equivalent to 0.5 g creatine was dissolved in 200 ml of the Aloe Vera juice solutions. Initial samples were retained and stored frozen. The remainder were divided into two aliquots of 100 ml, one aliquot was stored at ambient temperature 21° C. and one aliquot at +4° C. Samples were removed at various intervals and stored in a freezer (−20° C.).

Samples of Aloe Vera were diluted 31 times and 20 μl added to 900 μl of reagent 1 (MPRI Creatinine PAP assay; Boehringer Mannheim). Color development was read at 547 nm using semi-micro cuvettes in a Shimatzu photometer. The concentration of creatine was calculated by reference to a standard curve obtained using serial dilutions of 10 mM creatine in water.

The results are shown in Table 1 and Table 2. At room temperature creatine concentrations in the Aloe Vera drinks was unchanged up to 3 hours and the losses of creatine up to 24 hours were small. Stability was greater with Herbal Lemon than the Natural Aloe Vera drink. After several weeks there was a substantial and progressive loss of creatine in the drinks and at six weeks only about one third was left. The greatest deterioration occurred in Natural Aloe Vera. At 4° C. at least 85% creatine was retained at six weeks. In both the Berry and Herbal Lemon flavors the retention was 90%. With the natural flavor it was 85%.

It is concluded, that at an acidic pH at which Aloe Vera is available, the losses of creatine over 24 hours is relatively small, and it is beneficial to consume freshly made creatine-Aloe Vera drinks during this period. However, it is not prudent to store creatine-Aloe Vera drinks for much longer than 24 hours at room temperature. It is preferred instead to store the drinks in a refrigerator. There is a very substantial loss of creatine after several weeks at room temperature but not at +4° C.

TABLE 1

The stability of creatine in Aloe Vera drinks stored at ambient temperature (20° C.)

| Aloe Vera Drink | Percentage Creatine Remaining | | | | | | | |
|---|---|---|---|---|---|---|---|---|
| | (hours) | | | | | (days) | | |
| | 0 | 3 | 6 | 10 | 24 | 14 | 28 | 42 |
| Herbal Lemon | 100 | 102 | 98.8 | 98.2 | 93.3 | 69.6 | 50.4 | ND |
| Natural | 100 | 100 | 94.6 | 91.7 | 86.2 | 55.3 | 36.2 | 35.1 |
| Berry | 100 | ND | ND | ND | ND | 62.9 | 47.0 | 9.4 |

ND = Not done

TABLE 2

The stability of creatine in Aloe Vera drinks stored in a refrigerator (+4° C.)

| Aloe Vera Drink | Percentage Creatine Remaining Time (days) | | | |
|---|---|---|---|---|
| | 0 | 14 | 28 | 42 |
| Herbal Lemon | 100 | 90.1 | 91.2 | 91.2 |
| Natural | 100 | 92.6 | 86.6 | 85.5 |
| Berry | 100 | 95.4 | 92.0 | 92.7 |

What is claimed is:

1. An acidic creatine-containing composition for human consumption, s composition being unflavored or fruit flavored comprising Aloe Vera extract.

2. A composition according to claim 1, wherein said creatine is substantially stable at ambient temperature or below.

3. A composition according to claim 1, wherein said Aloe Vera extract in said composition comprises from 10 to 90% v/v Aloe Vera juice.

4. A composition according to claim 1, wherein said composition has a pH in the range 2.5 to 6.5.

5. A composition according to claim 1 in which the composition has a pH in the range 3.0 to 6.0.

6. A composition according to claim 1 comprising at least one member selected from the group consisting of vitamins, lipids, carbohydrates, amino acids, trace elements, colorings, flavors, artificial sweeteners, natural health improving substances, antioxidants, stabilizers, preservatives and buffers.

7. A composition according to claim 1 provided as unitary doses.

8. A method of making a creatine-composition according to claim 1, the method comprising: providing stable creatine; and mixing said creatine with an Aloe Vera extract to form an acidic mixture thereof.

9. A method of making a creatine-composition according to claim 8, 10 further comprising packaging said mixture.

10. A method of storing a creatine-containing composition for human consumption, the method comprising: forming an acidic mixture comprising creatine and Aloe Vera extract; and storing said composition at or below ambient temperature.

11. The method according to claim 8, further comprising storing said composition below ambient temperature.

12. A method according to claim 8, further comprising storing said composition at 0° to 8° C.

13. A method of storing a creatine-containing composition for human consumption, the method comprising: forming an acidic mixture comprising creatine and Aloe Vera extract; and drying said composition to form a stable powder.

14. The method of claim 13, further comprising packaging the mixture.

15. An acidic creatine-containing composition for human consumption, said composition being unflavored or fruit flavored and suspended in an edible form.

16. A composition according to claim 15, further comprising an Aloe Vera extract.

17. A method of supplying a creatine and Aloe Vera extract containing composition for human consumption, the method including providing a creatine and Aloe Vera extract containing acidic composition as a dry, stable powder, said powder when mixed with water or a suitable aqueous solution forming an acidic drink comprising physiologically effective quantities of creatine, wherein said creatine is substantially stable.

* * * * *